US008926623B2

(12) United States Patent
Trieu et al.

(10) Patent No.: US 8,926,623 B2
(45) Date of Patent: Jan. 6, 2015

(54) SYSTEM AND METHOD FOR FORMING POROUS BONE FILLING MATERIAL

(75) Inventors: Hai H. Trieu, Cordova, TN (US); Aashiish Agnihotri, Memphis, TN (US); Joseph Saladino, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 2025 days.

(21) Appl. No.: 11/622,570

(22) Filed: Jan. 12, 2007

(65) Prior Publication Data
US 2008/0172059 A1 Jul. 17, 2008

(51) Int. Cl.
*A61B 17/58* (2006.01)
*A61L 27/56* (2006.01)
*A61B 17/88* (2006.01)
*A61B 17/70* (2006.01)
*B01F 5/06* (2006.01)

(52) U.S. Cl.
CPC .............. *A61L 27/56* (2013.01); *A61L 2400/06* (2013.01); *B01F 2005/0636* (2013.01); *A61B 17/8833* (2013.01); *A61B 17/70* (2013.01)
USPC .......................................................... 606/94

(58) Field of Classification Search
USPC ................. 606/92–94; 623/17.11–17.16
See application file for complete search history.

(56) References Cited

U.S. PATENT DOCUMENTS

| | | |
|---|---|---|
| 5,047,031 A | 9/1991 | Constantz |
| 5,525,148 A | 6/1996 | Chow et al. |
| 5,650,108 A | 7/1997 | Nies et al. |
| 5,795,922 A | 8/1998 | Demian et al. |
| 5,820,632 A | 10/1998 | Constantz et al. |
| 6,083,264 A | 7/2000 | Wood et al. |
| 6,479,565 B1 | 11/2002 | Stanley |
| 6,547,866 B1 * | 4/2003 | Edwards et al. ............... 106/35 |
| 6,726,691 B2 | 4/2004 | Osorio et al. |
| 7,381,262 B2 * | 6/2008 | Tas ................................ 106/690 |
| 7,621,963 B2 * | 11/2009 | Simon et al. ............... 623/23.61 |

(Continued)

OTHER PUBLICATIONS

A. Boger, S. Verrier, M. Bohner, P. Heinz, E. Schneider; Properties of an injectable low modulus PMMA bone cement for vertebroplasty; European Cells and Materials vol. 10. Suppl. 1, 2005 (p. 17); AO Research Institute, Davos, Switzerland.

(Continued)

*Primary Examiner* — Christopher Beccia
(74) *Attorney, Agent, or Firm* — Sorell Lenna & Schmidt LLP

(57) ABSTRACT

A method for treating a vertebral bone comprises providing a gaseous substance and providing a flowable and settable bone filling material. The method further comprises introducing the gaseous substance into the bone filling material to form a porous bone augmentation material and inserting a material delivery device into the vertebral bone. The method further comprises injecting the porous bone augmentation material from the material delivery device and into the vertebral bone.

24 Claims, 3 Drawing Sheets

(56) References Cited

U.S. PATENT DOCUMENTS

| | | | |
|---|---|---|---|
| 2002/0018796 A1* | 2/2002 | Wironen | 424/423 |
| 2005/0059979 A1 | 3/2005 | Yetkinler et al. | |
| 2005/0197422 A1 | 9/2005 | Mayadunne et al. | |
| 2005/0220771 A1* | 10/2005 | Deslauriers et al. | 424/93.7 |
| 2006/0095138 A1 | 5/2006 | Truckai et al. | |
| 2006/0122614 A1 | 6/2006 | Truckai et al. | |
| 2006/0122625 A1 | 6/2006 | Truckai et al. | |
| 2006/0195115 A1 | 8/2006 | Ferree | |
| 2006/0233851 A1* | 10/2006 | Simon et al. | 424/422 |
| 2007/0191963 A1* | 8/2007 | Winterbottom et al. | 623/23.5 |
| 2007/0213717 A1 | 9/2007 | Trieu et al. | |
| 2007/0213718 A1 | 9/2007 | Trieu | |
| 2007/0213822 A1 | 9/2007 | Trieu | |
| 2007/0213823 A1 | 9/2007 | Trieu | |
| 2007/0213824 A1 | 9/2007 | Trieu | |
| 2008/0103564 A1* | 5/2008 | Burkinshaw et al. | 607/96 |

OTHER PUBLICATIONS

A. Boger, P. Heinz, M. Bohner, E. Schneider; Vertebral Cancellous Bone Augmented with Stiffness-adapted PMMA Cement does not Show Acute Failure under Dynamic Loading; European Cells and Materials vol. 11. Suppl. 1, 2006 (p. 29); AO Research Institute, Davos, Switzerland.

Boger, A., et al. "Properties of an Injectable Low Modulus PMMA Bone Cement for Vertebroplasty," European Cells and Materials, vol. 10, Suppl. 1, p. 17 (2005).

Iooss et al., A new injectable bone substitute combining poly (ε-caprolactone) microparticles with biphasic calcium phosphate granules. Biomaterials 22 (2001) 2785-2794.

\* cited by examiner

SYSTEM AND METHOD FOR FORMING POROUS BONE FILLING MATERIAL

CROSS REFERENCE

The related applications, incorporated by reference herein are:

U.S. Utility patent application Ser. No. 11/622,558, filed on Jan. 12, 2007 and entitled "System and Method for Pressure Mixing Bone Filling Material" and U.S. Utility patent application Ser. No. 11/622,547, filed on Jan. 12, 2007 and entitled "System and Method For Forming Bone Filling Materials With Microparticles".

BACKGROUND

Bone cements and other bone filling materials are currently used throughout the skeletal system to augment or replace bone weakened or lost to disease or injury. One example of a treatment that includes the administration of bone filling material is vertebroplasty. During vertebroplasty, the cancellous bone of a vertebral body is supplemented with bone filling material. Frequently, the available bone filling materials do not possess material properties similar to the native bone. Materials, systems, and methods are needed to form and deliver bone filling materials that may be selectively matched to the natural bone undergoing treatment.

SUMMARY

In one embodiment, a method for treating a vertebral bone comprises providing a gaseous substance and providing a flowable and settable bone filling material. The method further comprises introducing the gaseous substance into the bone filling material to form a porous bone augmentation material and inserting a material delivery device into the vertebral bone. The method further comprises injecting the porous bone augmentation material from the material delivery device and into the vertebral bone.

In another embodiment a bone augmentation system comprises a first vessel at least partially filled with a gaseous substance and a second vessel at least partially filled with a flowable and settable bone filling material. The system further comprises a mixing vessel in fluid communication with both the first and second vessels to receive the gaseous substance and the flowable and settable bone filling material. The mixing vessel includes a mixing mechanism for mixing the gaseous substance and the bone filling material to form a bone augmentation material. The system also includes a dispensing instrument comprising a dispensing reservoir for receiving the bone augmentation material and comprising a cannulated member adapted to deliver the bone augmentation material into a body region adjacent cancellous bone.

A method of augmenting a bone comprises pressurizing a gaseous substance, mixing the gaseous substance and a flowable bone filling material to form a bone augmentation material, injecting the bone augmentation material into the bone, and allowing the bone augmentation material to set to a hardened and porous condition within the bone.

Additional embodiments are included in the attached drawings and the description provided below.

DETAILED DESCRIPTION

Figure 1:
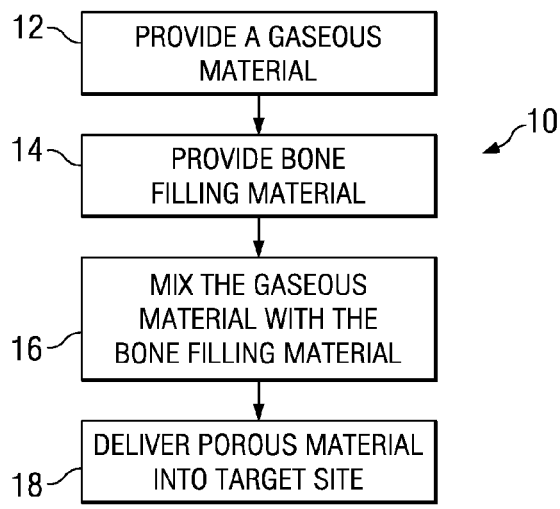
FIG. 1 is a flowchart for a process of forming a modulated bone augmentation material according to one embodiment of the disclosure.

The present disclosure relates generally to devices, methods and apparatus for augmenting bone, and more particularly, to methods and instruments for augmenting bone with a porous material. For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 2:
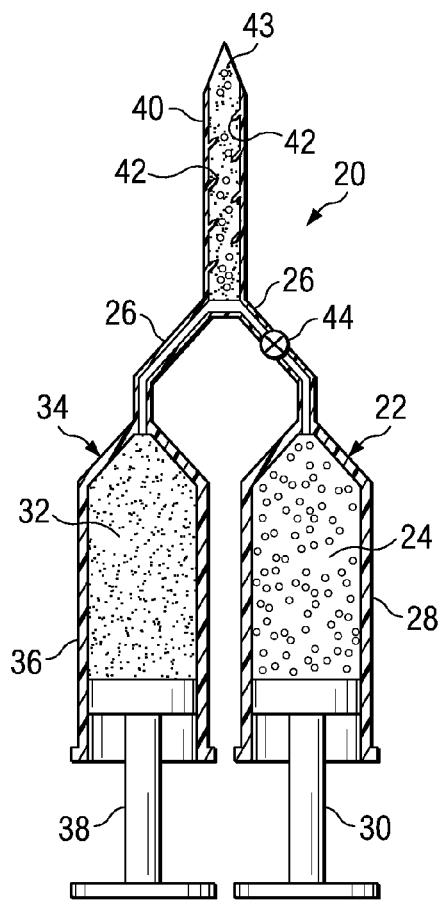
FIG. 2 is a cross-sectional view of a material preparation system according to one embodiment of the present disclosure.

Referring first to FIG. 1, the reference numeral 10 refers to a method for forming a modified or modulated bone augmentation material that may better correspond to the material properties, including the modulus of elasticity, of a target bone region as compared to unmodulated bone filling material such as bone cement. At step 12, a gaseous substance may be provided to a material preparation system 20 as shown in FIG. 2. Specifically, a vessel 22 may be filled with a gaseous substance 24 such as air. The vessel 22 may be connected, either releasably or fixedly, to connective tubing 26. In this embodiment, the vessel 22 has a syringe-like configuration, comprising a reservoir 28 which contains the gaseous substance 24 and a plunger 30 which may be moved through the reservoir 28 to pressurize the gaseous substance and to dispense the gaseous substance through the connective tubing 26. It is understood that in alternative embodiments, the contents of the vessel may be pressurized by any known means or alternatively, the gaseous substance may be provided in prepackaged, pressurized form such as a compressed gas, such as carbon dioxide, nitrogen, or oxygen (as will be described below).

Referring again to the method 10 of FIG. 1, at step 14, an appropriate bone filling material may be selected. Suitable bone filling materials may include polymethylmethacrylate (PMMA) bone cement, calcium phosphate bone cement, calcium sulfate compounds, calcium aluminate compounds, aluminum silicate compounds, hydroxyapatite compounds, in situ curable ceramics or polymers, or other flowable materials that become more rigid after delivery. Generally, before it is modified, the bone filling material may have a higher modulus of elasticity than the target bone region. The bone filling material may be provided as multiple components such as, a PMMA powder and a PMMA monomer. In FIG. 1, the order in which the gaseous substance and the bone filling material are introduced is merely exemplary, and it is understood that the bone filling material may be introduced first or contemporaneously with the introduction of the gaseous material.

Referring again to FIG. 2, a bone filling material 32, which in this embodiment is a bone cement, may be provided to the material preparation system 20. Specifically, a vessel 34 may be filled with the bone filling material 32. The vessel 34 may be connected, either releasably or fixedly, to the connective tubing 26. In this embodiment, the vessel 34 has a syringe-like configuration, comprising a reservoir 36 which contains the bone filling material 32 and a plunger 38 which may be moved through the reservoir 36 to dispense the bone filling material 32 through the connective tubing 26. It is understood that in alternative embodiments, the contents of the vessel may be pressurized by any known means or alternatively, the gaseous substance may be provided in prepackaged, pressurized form.

Referring again to FIGS. 1 and 2, at step 16 the gaseous substance 24 may flow through the connective tubing 26 and into a mixing vessel 40 where it becomes introduced into the liquid bone filling material 32 which has traveled through the tubing 26 from the vessel 34. In this embodiment, the mixing vessel 40 may be a static mixer comprising fixed mixing elements 42. As the two flow streams of gas 24 and bone filling material 32 move through the static mixer 40, buffeted by the mixing elements 42, bubbles of the gaseous substance 24 may form within and become dispersed throughout the bone filling material 32 to form a porous modulated bone augmentation material 43. The gaseous substance 24 may be added until the concentration of bubbles in the liquid bone augmentation material 43 is sufficient to lower the overall modulus of elasticity of the final cured or hardened modulated bone augmentation material to a level that more closely matches the modulus of the target bone region or that at least reduces the risk of damage to the adjacent bone that could otherwise be caused by the unmodulated bone cement. In certain patients, it may be desirable to reduce the modulus of elasticity to a level lower than natural cancellous bone. For example, a modulus of elasticity for hardened bone augmentation material that is less than five times that of cancellous bone may be suitable for some patients.

In alternative embodiments, a more active form of mixing may be used. For example, the mixing vessel may comprise an agitator for mixing the gaseous substance and the bone filling material. Alternatively, a gas diffuser or aerator may be used to disperse the gaseous substance throughout the bone filling material.

In the embodiment of FIG. 2, the material preparation system 20 may further include a control mechanism 44, such as a valve, to control the flow of the gaseous substance 24 into the mixing vessel 40. With the valve 44 in an open position, a continuous flow of gaseous substance 24 may be dispensed from the vessel 22 into the mixing vessel 40. The valve 44 may also be toggled between open and closed positions to provide intermittent bursts of gas flow. Further, the valve 44 may be used to control the velocity of the flowing gaseous substance 24 and the pressure within the vessel 22.

Thus, by controlling the continuity, rate, and pressure of the gaseous phase substance 24, the control valve 44 may be used to control the size and density of the bubbles that form in the fluid modulated bone augmentation material, and ultimately the size and density of the pores that are formed in the hardened modulated bone augmentation material. For example, larger pores may impart a lower modulus than the same quantity of smaller pores. A higher density of pores may impart a lower modulus to the bone filling material than would a less dense array of pores of the same size and material properties.

The desired size and density of the pores may be dependent upon the size of the target bone region and characteristics of the patient including the age, bone density, body mass index, or health of the patient. For example, an elderly osteoporotic vertebroplasty patient may require a more reduced modulus bone augmentation material than would a young healthy trauma victim undergoing a similar procedure. The size of the pores may be selected based upon the patient and controlled by pressurization, flow rate, a pattern of intermittent introduction of the gaseous substance, or other means. For example, 90% of the pores may be in the range of 1 to 2000 microns in diameter. Other suitable pore sizes may range from 10 to 1000 microns.

Other additives may be added to the bone filling material during the preparation of the bone filling material or during the mixing of the gaseous substance. Additives that include radiocontrast media may be added to the bone filling material to aid in visualizing the bone augmentation material with imaging equipment. Suitable radiocontrast materials may include barium sulfate, tungsten, tantalum, or titanium. Osteoconductive or osteoinductive materials may be added to promote bone growth into the hardened bone augmentation material. Suitable osteoconductive materials may include hydroxyapatite (HA), tricalcium phosphate (TCP), HA-TCP, calcium phosphate, calcium sulfate, calcium carbonate, and/or bioactive glasses. Suitable osteoinductive materials may include proteins from transforming growth factor (TGF) beta superfamily, or bone-morphogenic proteins, such as BMP2 or BMP7. Pharmacological agents may be added to promote healing and prevent or fight infection. Suitable pharmacological additives may include antibiotics, anti-inflammatory drugs, or analgesics.

Referring again to FIG. 1, at step 18, the modulated bone augmentation material may be delivered into a target bone region in a patient's anatomy. The modulated bone augmentation material may be transferred to a delivery system, such as a syringe or a threaded material dispensing system prior to delivery into the target bone region. In alternative embodiments, the bone filling material and the gaseous substance may be mixed in the same container that will be used to dispense the mixture such that a material transfer becomes unnecessary. In still another alternative embodiment, a gas cartridge can be directly attached to the delivery nozzle of a known bone cement delivery instrument.

Although the target bone region will often be in a bone, other bone regions, such as joints, may receive the modulated bone augmentation material to, for example, promote fusion. Examples of target bone regions may be fractured cortical or cancellous bone, osteoporotic cancellous bone, or degenerated intervertebral discs. By matching the modulated bone augmentation material to the material properties of the adjacent bone, complications associated with unaltered, high modulus bone cements may be minimized. In particular, matching the material properties may provide a uniform stress distribution, minimizing significant stress concentrations that may pose a fracture risk to adjacent bone.

Figure 3:
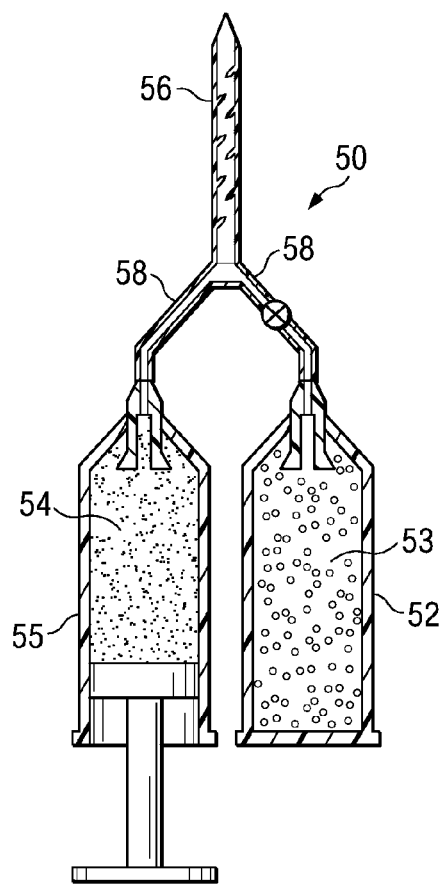
FIG. 3 is a cross-sectional view of a material preparation system according to another embodiment of the present disclosure.

Referring now to FIG. 3, in an alternative embodiment, a material preparation system 50 may be substantially similar to the system 20 with the differences to be described. In this embodiment, a vessel 52 may be filled with a compressed gaseous substance 53 such as carbon dioxide. As described above in method 10, the gaseous substance 53 may flow into a mixing vessel 56 where it may be dispersed throughout a bone filling material 54 from a vessel 55. The vessel 52 may be removable from connective tubing 58 through the use of quick-connect fasteners, threaded fasteners, clamp fasteners, or other suitable fasteners. Thus, the gaseous substance 53 may be provided in a pre-measured, pre-filled, pre-pressurized interchangeable cartridge format that may simplify the bone augmentation material preparation process.

Figure 4:
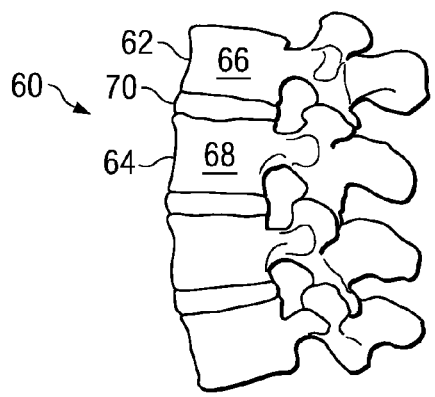
FIG. 4 is a sagittal view of a section of a vertebral column.

Referring now to FIG. 4, in one embodiment, a modulated bone augmentation material formed by method 10 may be used to augment or replace portions of a vertebral column. The reference numeral 60 refers to a healthy vertebral joint section of a vertebral column. The joint section 60 includes adjacent vertebrae 62, 64 having vertebral bodies 66, 68, respectively. An intervertebral disc 70 extends between the vertebral bodies 66, 68. Although FIG. 4 generally depicts a lumbar region of the spine, it is understood that the systems, materials, and methods of this disclosure may be used in other regions of the vertebral column including the thoracic or cervical regions.

Figure 5:
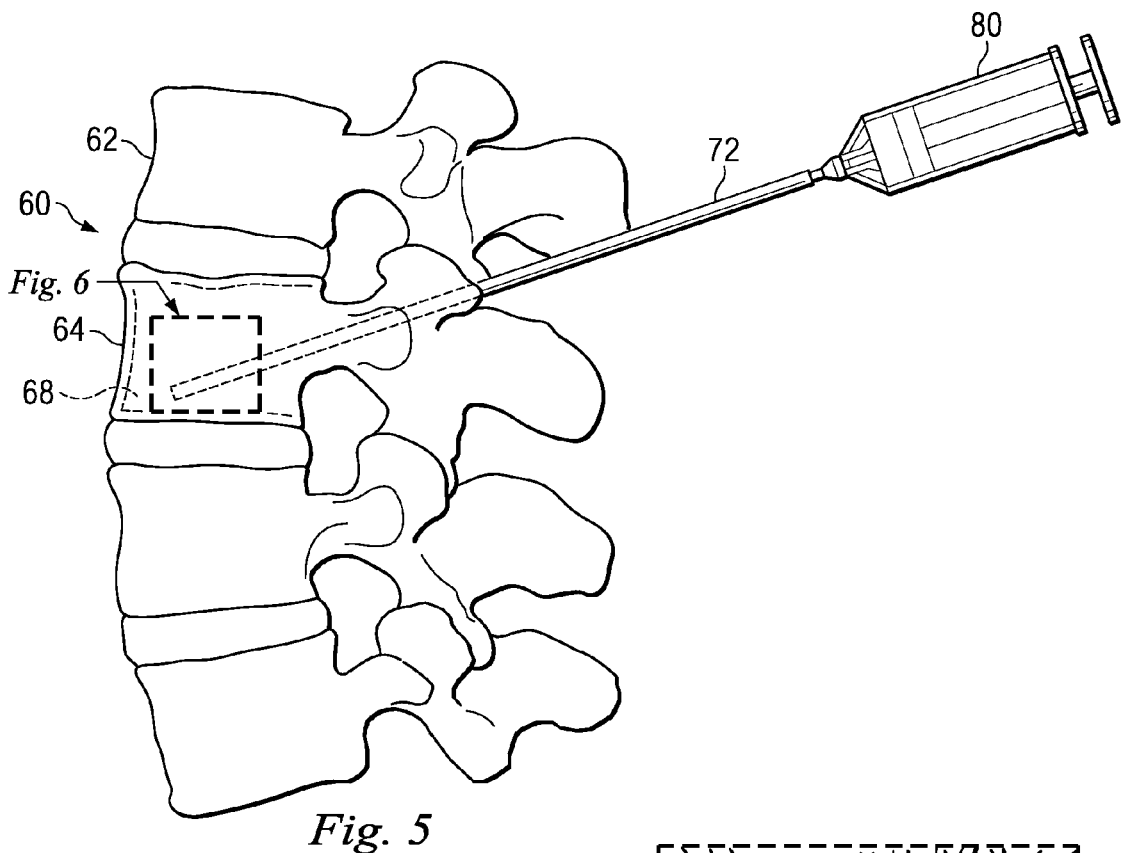
FIG. 5 is a sagittal view of a section of a vertebral column undergoing a vertebroplasty procedure using a porous bone augmentation material.
Figure 6:
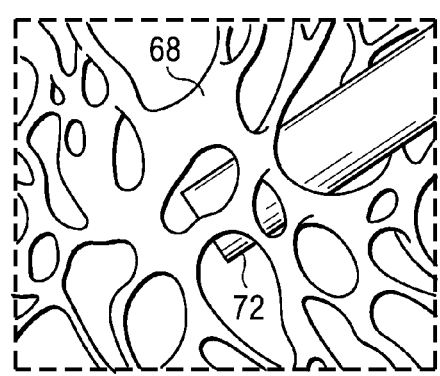
FIGS. 6-7 are detailed views of the procedure of FIG. 5.
Figure 7:
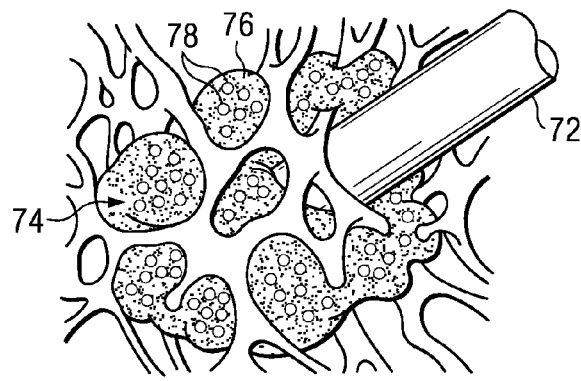
Figure 8:
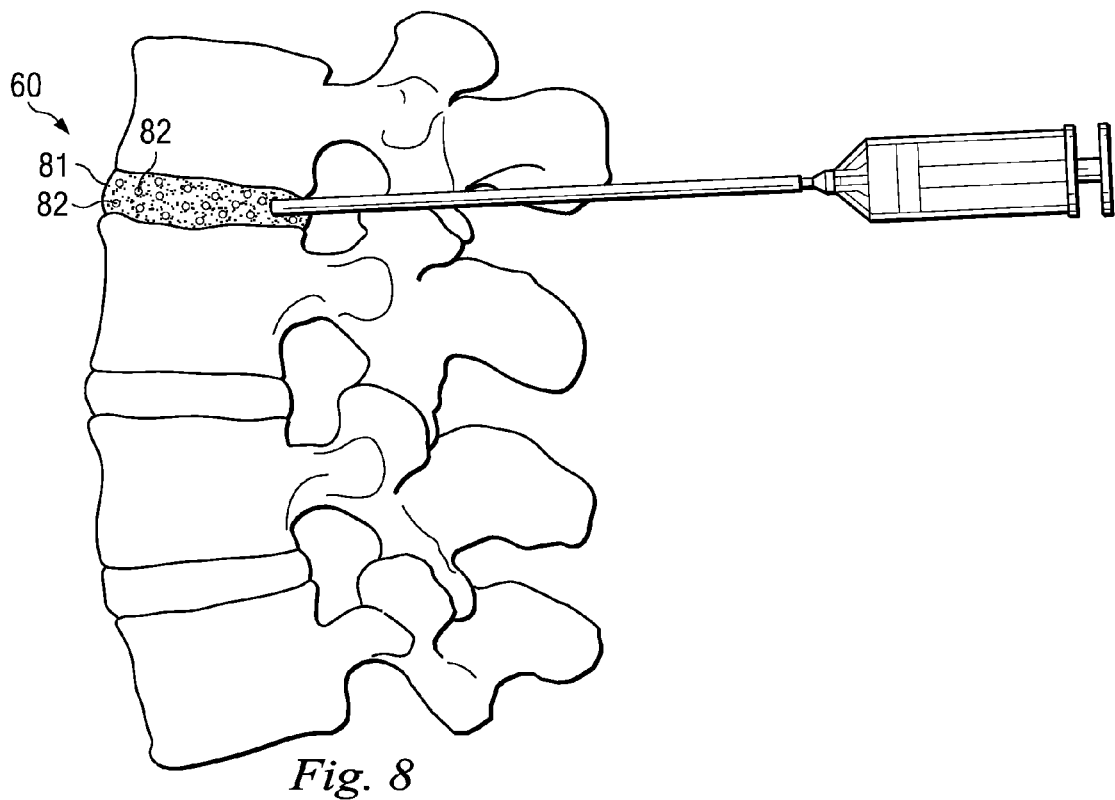
FIG. 8 is a sagittal view of a section of a vertebral column with an intervertebral disc treated with porous bone filling material.

Referring now to FIGS. 5-7, due to traumatic injury, cancer, osteoporosis or other afflictions, the vertebral body portion 68 of the vertebra 64 may begin to collapse, causing pain and loss of bone height. One procedure for restoring the vertebral height, reducing pain, and/or building mass is known as vertebroplasty. In a vertebroplasty procedure according to one embodiment of this disclosure, a stylet or other sharpened instrument (not shown) may be inserted into an injection instrument such as a cannula 72 and arranged so that a sharpened tip protrudes through the end of the cannula. The assembled stylet and cannula 72 may then be inserted through a pedicle of the vertebra 64 and into the cancellous bone of the vertebral body 68. This insertion may be guided through the use of fluoroscopy or other imaging modalities. With the cannula 72 in place in the vertebral body 68, the stylet may be withdrawn leaving the cannula in place to serve as a pathway for delivering instruments or materials into the bone. In alternative embodiments, a surgical needle having a cannulated body and a pointed tip may be used to access the vertebral body.

Following the method 10, described above, a modulated bone augmentation material 74 comprised of bone cement 76 and bubbles of gaseous substance 78 may be formed and transferred to a delivery system 80. The delivery system 80 may be a conventional syringe, having a material reservoir and a plunger mechanism movable therethrough, or a more sophisticated threaded injection system such as the type covered by, for example, U.S. Pat. No. 6,348,055 which is incorporated by reference herein. Other types of material delivery systems may also be suitable. The delivery system 80 may be actuated, such as by moving the plunger mechanism into the material reservoir, to move the bone augmentation material 74 through the cannula 72 and into the vertebra 64 where the mixture may flow into the interstices of the cancellous bone of the vertebral body 68 as shown in FIG. 7. It is understood that the bubbles of gaseous substance 78 shown in FIG. 7 are not necessarily to scale but rather are merely exemplary of the random disbursement of the bubbles of gaseous substance which will later form pores within the hardened bone augmentation material. As described above, within any given mixture of modulated bone augmentation material, the pores may have different sizes and/or properties. Further, the density of pores may be determined based upon the amount the original bone filling material must be modified to achieve an acceptable modulated bone augmentation material.

With the bubbles of gaseous substance 78 distributed throughout the bone cement 76, the modulated bone augmentation material 74 may be cured or otherwise allowed to harden within the vertebral body 68. The bubbles of gaseous substance 78 may remain suspended in the hardened bone cement 76, forming pores which reduce the overall stiffness of the modulated bone augmentation material 74. The modulus of elasticity of the hardened modulated bone augmentation material 74 may be lower than that of the unmodulated hardened bone filling material 76, alone, and closer to the modulus of elasticity of the cancellous bone of the vertebral body 68 than that of the hardened bone filling material alone. Thus, the material 74 creates a more uniform stiffness in the vertebral body 68, avoiding the significant alterations in stress distribution that would be associated with the use of bone cement alone. The more uniform stiffness in the vertebral body 68 may lower the risk for fracture in the adjacent vertebrae.

Although the use of the modulated bone augmentation material 74 has been described for use in a vertebroplasty procedure, it is understood that in alternative treatments, channels or voids may be formed in the vertebral body using probes, balloons, drills, cutting blades or other devices. In these embodiments, the mixture of gaseous bubbles and bone filling material may be used to fill the preformed voids or channels. The resulting reduced modulus material may be particularly effective in these embodiments as the otherwise unmodulated, large concentrations of bone cement accumulating in the preformed voids may give rise to significant alteration is the stress distribution.

Although the use of modulated bone augmentation material has been described primarily for vertebral body applications, it is understood that the same modulated material may be used for other procedures where reduced modulus bone cement may be desirable. For example, the modulated material may be useful for fracture repair.

In one alternative embodiment, a modulated bone augmentation material 81, including gaseous bubbles 82, may be created using the method 10 and may be used to fuse the joint section 60. The fusion of the joint 60 may be accomplished using conventional fusion techniques including transforaminal lumbar interbody fusion (TLIF), posterior lumbar interbody fusion (PLIF), or anterior lumbar interbody fusion (ALIF) procedures. Such techniques may involve the use of cages or other intervertebral spacers to maintain the height of the disc space. As a supplement or replacement for the bone graft or bone cement that would otherwise be used in a spinal fusion procedure, the modulated material 81 may be injected into the disc 70 or the disc space remaining after the removal of disc 70. The modulated material 81 may flow into crevices, voids, or prepared areas of the adjacent vertebral endplates. After hardening, the material 81 may have a modulus of elasticity similar to that of the adjacent endplates of the vertebrae 62, 64, or at least lower than unmodulated bone cement. Use of the modulated material 81 may reduce the risk of the hardened material subsiding into the endplates of the adjacent vertebrae 62, 64.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "anterior," "posterior," "superior," "inferior," "upper," and "lower" are for illustrative purposes only and can be varied within the scope of the disclosure. In the claims, means-plus-function clauses are intended to cover the elements described herein as performing the recited function and not only structural equivalents, but also equivalent elements.

What is claimed is:

1. A method for treating a vertebral bone comprising: providing a pressurized gaseous substance; providing a flowable and settable bone filling material;
introducing the gaseous substance into the bone filling material to form a porous bone augmentation material by mixing the gaseous substance and the bone filling material in a static mixer to form the porous bone augmentation material, the static mixer comprising a plurality of projections extending from an inner surface of the static mixer configured to disperse the gaseous substance throughout the bone filling material, wherein the gaseous substance is added until a concentration of bubbles in the bone augmentation material is sufficient to lower the overall modulus of the bone augmentation material when in a hardened state, and the modulus is less than five times that of cancellous bone; inserting a material delivery device into the vertebral bone; injecting the porous bone augmentation material from the material delivery device and into the vertebral bone; and providing cure conditions to the bone augmentation material to set to the hardened and porous condition within the bone, wherein 90% of the pores in the augmentation material are in a range of 1 to 2000 microns in diameter.

2. The method of claim 1 wherein the gaseous substance is air.

3. The method of claim 1 wherein the gaseous substance is carbon dioxide.

4. The method of claim 1 wherein the step of introducing the gaseous substance comprises intermittently introducing the gaseous substance.

5. The method of claim 1 further comprising controlling a flow rate of the gaseous substance.

6. The method of claim 1 further comprising controlling the pressure of the gaseous substance.

7. The method of claim 1 wherein the flowable and settable bone filling material comprises polymethylmethacrylate.

8. The method of claim 1 wherein the flowable and settable bone filling material comprises calcium phosphate.

9. The method of claim 1 wherein the flowable and settable bone filling material comprises calcium sulfate.

10. The method of claim 1 wherein the flowable and settable bone filling material comprises hydroxyapatite.

11. The method of claim 1 further comprising forming a void in the vertebral bone prior to the step of injecting.

12. The method of claim 1 wherein the porous bone augmentation material has a lower modulus of elasticity than the bone filling material when hardened.

13. The method of claim 1 further comprising injecting the porous bone augmentation material from the injection device and into an intervertebral disc space adjacent the vertebral bone.

14. The method of claim 1 further comprising mixing the gaseous substance and the bone filling material.

15. The method of claim 1 wherein the step of introducing comprises agitating the gaseous substance and the bone filling material to form the porous bone augmentation material.

16. The method of claim 1 wherein the step of introducing comprises diffusing the gaseous substance in the bone filling material with a gas diffuser to form the porous bone augmentation material.

17. The method of claim 1 wherein the bone augmentation material includes a radiocontrast media.

18. The method of claim 1 wherein the bone augmentation material includes an osteoconductive material.

19. The method of claim 1 wherein the bone augmentation material includes an osteoinductive material.

20. The method of claim 1 wherein the bone augmentation material includes a pharmacological agent.

21. The method of claim 11 wherein each of the plurality of voids is between 1 and 2000 microns in diameter.

22. A method of augmenting a bone comprising pressurizing a gaseous substance, mixing the pressurized gaseous substance and a flowable bone filling material to form a bone augmentation material by mixing the gaseous substance and the bone filling material in a static mixer to form the porous bone augmentation material, the static mixer comprising a plurality of projections extending from an inner surface of the static mixer configured to disperse the gaseous substance throughout the bone filling material, wherein the gaseous substance is added until a concentration of bubbles in the bone augmentation material is sufficient to lower the overall modulus of the bone augmentation material when in a hardened state, and the modulus is less than five times that of cancellous bone, injecting the bone augmentation material into the bone, and providing cure conditions to the bone augmentation material to set to the hardened and porous condition within the bone, wherein the bone augmentation material is porous and 90% of the pores are in a range of 1 to 2000 microns in diameter.

23. The method of augmenting a bone of claim 22 further wherein the bone is cancellous bone.

24. The method of augmenting a bone of claim 22 wherein the bone filling material in a hardened state has a modulus of elasticity greater than the bone augmentation material in a hardened state.

* * * * *